United States Patent
Mogna et al.

(10) Patent No.: US 12,329,791 B2
(45) Date of Patent: *Jun. 17, 2025

(54) MIXTURE OF PROBIOTIC BACTERIA STRAINS FOR USE IN THE TREATMENT OF ALLERGIC ASTHMA AND WITH RECURRENT WHEEZING, PREFERABLY IN PAEDIATRIC SUBJECTS

(71) Applicant: PROBIOTICAL S.P.A., Novara (IT)

(72) Inventors: Vera Mogna, Novara (IT); Marco Pane, Novara (IT); Angela Amoruso, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 557 days.

This patent is subject to a terminal disclaimer.

(21) Appl. No.: 17/436,847

(22) PCT Filed: Mar. 6, 2020

(86) PCT No.: PCT/IB2020/051961
§ 371 (c)(1),
(2) Date: Sep. 7, 2021

(87) PCT Pub. No.: WO2020/178794
PCT Pub. Date: Sep. 10, 2020

(65) Prior Publication Data
US 2022/0175855 A1    Jun. 9, 2022

(30) Foreign Application Priority Data
Mar. 7, 2019    (IT) ........................ 102019000003351

(51) Int. Cl.
| | |
|---|---|
| *A61K 35/745* | (2015.01) |
| *A61K 35/74* | (2015.01) |
| *A61P 11/00* | (2006.01) |
| *A61P 11/06* | (2006.01) |
| *A61K 35/747* | (2015.01) |

(52) U.S. Cl.
CPC ............ *A61K 35/745* (2013.01); *A61K 35/74* (2013.01); *A61P 11/00* (2018.01); *A61P 11/06* (2018.01); *A61K 35/747* (2013.01)

(58) Field of Classification Search
CPC ....... A61K 35/745; A61K 35/74; A61P 11/06; A61P 37/08; A61P 11/00; C12N 1/20
See application file for complete search history.

(56) References Cited

U.S. PATENT DOCUMENTS

| | | | |
|---|---|---|---|
| 9,185,927 B2 * | 11/2015 | Mogna ................... | A23L 33/135 |
| 9,498,503 B2 | 11/2016 | Mogna et al. | |
| 9,931,363 B2 | 4/2018 | Mogna et al. | |
| 2015/0017142 A1 | 1/2015 | Mogna et al. | |
| 2024/0216449 A1 | 7/2024 | Mogna et al. | |

FOREIGN PATENT DOCUMENTS

| | | |
|---|---|---|
| CN | 103037876 A | 4/2013 |
| CN | 103748213 A | 4/2014 |
| CN | 104800247 A | 7/2015 |
| KR | 20180118273 A | 10/2018 |
| WO | 2011/110918 A1 | 9/2011 |
| WO | 2011/149345 A1 | 12/2011 |
| WO | 2013/050833 A1 | 4/2013 |
| WO | WO-2017208172 A1 * | 12/2017 ........... A61K 31/365 |

OTHER PUBLICATIONS

Lee et al., Excerpt of "Handbook of Probiotics and Prebiotics", Second Edition, 2009, John Wiley and Sons, Inc., Hoboken, New Jersey, p. 399. Total of 3 pages, On IDS filed Apr. 3, 2024. (Year: 2009).*
Bozzi Cionci et al., 2018 "Therapeutic microbiology: the role of Bifidobacterium breve as food supplement for the prevention/treatment of paediatric diseases." Nutrients, 10(11)1723, pp. 1-17; doi:10.3390/nu10111723 (Year: 2018).*
Drago et al. 2022. "The Probiotics in Pediatric Asthma Management (PROPAM) Study in the Primary Care Setting: A Randomized, Controlled, Double-Blind Trial with Ligilactobacillus salsalivarius LS01 (DSM 22775) and Bifidobacterium breve B632 (DSM 24706)" . Journal of Immunology Research (2022) (Year: 2022).*
First Notification of Office Action for Chinese Application No. 202080013938.0 on behalf of Probiotical S.P.A. on Mar. 6, 2020. Issued on Nov. 17, 2023. 9 pages. CN original and Eng translation.
Search Report for Chinese Application No. 202080013938.0 on behalf of Probiotical S.P.A. on Mar. 6, 2020. Issued on Nov. 14, 2023. 6 pages. CN original and Eng translation.
Ciprandi, G. et al., Probiotics in Children with Asthma. Children, (Jun. 29, 2022), 9, 978. 13 pages. Doi.org/10.3390/children9070978.
Ciprandi, G. et al., The Probiotics in Pediatric Asthma Management (PROPAM) Study. A Post Hoc analysis in allergic children. Ann Allergy Asthma Immunol., 2022, 129 (1); 2 pages. Epub Apr. 26, 2022. Website: doi.org/10.1016/j.anai.2022.04.026.
Ciprandi, G. et al., The PRObiotics in Pediatric Asthma Management (PROPAM) study: A post hoc analysis in preschoolers. Pediatric Pulmonology. (2022), 1-3. DOI:10.1002/ppul.25878.

(Continued)

*Primary Examiner* — Aaron J Kosar
*Assistant Examiner* — Andrew T Moehlman
(74) *Attorney, Agent, or Firm* — Steinfl + Bruno LLP

(57) ABSTRACT

An isolated strain of bacteria *Bifidobacterium breve* (B632) DSM 24706 and related mixtures, compositions and methods for treatment of a disorder or an ailment or a disease of the respiratory airways including asthma and dyspnoea are described. The composition comprising the mixture includes at least one physiologically and/or pharmacologically acceptable additive and/or technological excipient. The isolated strain mixture and composition can be administered to paediatric subjects having a disorder or an ailment or a disease of the respiratory airways.

10 Claims, 1 Drawing Sheet

(56) References Cited

OTHER PUBLICATIONS

Drago, L. et al. A post hoc analysis on the effects of a probiotic mixture on asthma exacerbation frequency in schoolchildren. ERJ Open Res, 2022; 8: 0002-2022. 4 pages. Published online May 9, 2022. DOI: 10.1183/23120541.00020-2022.

Drago, L. et al., Immunomodulatory Effects of Lactobacillus salivarius LS01 and Bifidobacterium breve BR03, Alone and in Combination, on Peripheral Blood Mononuclear Cells of Allergic Asthmatics. Allergy Asthma Immunol Res, (Jul. 2015), 7 (4), 409-413. Website: dx.doi.org.10.4168/aair.2015.7.4.409.

Drago, L. et al., The Probiotics in Pediatric Asthma Management (PROPAM) Study in the Primary Care Setting: A Randomized, Controlled, Double-Blind Trial with Ligilactobacillus salivarius LS01 (DSM 22775) and Bifidobacterium breve B632 (DSM 24706). Hindawi, Journal of Immunology Research, (Jan. 17, 2022), Article ID 3837418, 7 pages. Doi.org/10.1155/2022/3837418.

Lee, Y.K. et al., Excerpt of "Handbook of Probiotics and Prebiotics", Second Edition, 2009, John Wiley and Sons, Inc., Hoboken, New Jersey, p. 399. Total of 3 pages.

Bateman, E.D. et al. Global Strategy for Asthma Management and Prevention: GINA executive summary. Eur Respir J, 2008, 31: 143-178.

Bibbo, S. et al., The role of diet on gut microbiota composition European Review for Medical and Pharmacological Sciences 2016; 20: 4742-4749.

Communication pursuant to Rules 161(1) and 162 EPC for EPO 20716185.2 filed on behalf of Probiotical S.P.A. Mailed on Oct. 21, 2021. 3 pages.

Drago, L. et al. Immunomodulatory Effects of Lactobacillus salivarius LS01 and Bifidobacterium breve BR03, Alone and in Combination, on Peripheral Blood Mononuclear Cells of Allergic Asthmatics. Allergy Asthma Immunol Res. Jul. 2015; 7(4):409-413.

Indinnimeo, L. et al. Guideline on management of the acute asthma attack in children by Italian Society of Pediatrics, Italian Journal of Pediatrics, 2018, 44:46, 10 pages.

International Preliminary Report on Patentability for PCT/IB2020/051961 filed on Mar. 6, 2020 on behalf of Probiotical S.P.A. Mailed on Aug. 25, 2021. 8 pages.

International Search Report and Written Opinion for PCT/IB2020/051961 filed on Mar. 6, 2020 on behalf of Probiotical S.P.A. Mailed on May 29, 2020. 12 pages.

Nettis, E. et al., Probiotics and refractory chronic spontaneous urticaria, European Annals of Allergy and Clinical Immunology, vol. 48, No. 5, 182-187, Sep. 1, 2016.

Sirisinha, Stitaya: The potential impact of gut microbiota on your health: Current status and future challenges. Asian Pacific Journal of Allergy Immunol., Dec. 2016, 34 (4): 249-264.

Pulmonary Medicine Today, Feb. 2018, FCI21IT3705_82_3, pp. 233-234, Chinese Original and English Abstract. 5 pages.

Search Report of Office Action for Chinese Application No. 202080013938.0 on behalf of Probiotical S.P.A. on Mar. 6, 2020. Issued on Jul. 24, 2024. 4 pages. CN original and Eng translation.

Second Notification of Office Action for Chinese Application No. 202080013938.0 on behalf of Probiotical S.P.A. on Mar. 6, 2020. Issued on Jul. 25, 2024. 10 pages. CN original and Eng translation.

\* cited by examiner

MIXTURE OF PROBIOTIC BACTERIA STRAINS FOR USE IN THE TREATMENT OF ALLERGIC ASTHMA AND WITH RECURRENT WHEEZING, PREFERABLY IN PAEDIATRIC SUBJECTS

CROSS REFERENCE TO RELATED APPLICATIONS

The present application is the U.S. national stage of International Patent Application PCT/IB2020/051961 filed internationally on Mar. 6, 2020, which is herein incorporated by reference in its entirety and in turn, claims priority to Italian Patent Application No. 102019000003351 filed on Mar. 7, 2019.

The present invention regards an isolated strain of bacteria belonging to the species *Bifidobacterium breve* (B632) DSM 24706 for use in the treatment of a disorder (disturb) or an ailment (disordine) or a disease associated with an alteration of the respiratory airways and for use in the treatment of asthma and dyspnoea. Furthermore, the present invention further regards a mixture comprising or, alternatively, consisting of said isolated strain of probiotic bacteria, for use in the treatment of a disorder or an ailment or a disease associated with an alteration of the respiratory airways; for use in the treatment of asthma and dyspnoea. Furthermore, the present invention regards a composition comprising said mixture and, optionally, at least one physiologically and/or pharmacologically acceptable additive and/or technological excipient, for use in the treatment of a disorder or an ailment or a disease of the respiratory airways and for use in the treatment of asthma and dyspnoea. Said isolated strain, said mixture and said composition being validly administered and used in the treatment of paediatric subjects.

Asthma (GINA 2016 [1]; Global Initiative for Asthma) is a heterogeneous disease characterised by chronic airway obstruction. Asthma is defined by respiratory symptoms, such as dyspnoea or wheezing, shortness of breath, chest tightness and coughing which vary in intensity and duration along with airways flow limitation; asthma can be induced by numerous stimuli, including allergens, exposure to irritants, viruses, and physical exercise. At present, the aforementioned symptoms can be alleviated by bronchodilators, or antiinflammatory substances (for example glucocorticoid drugs). Asthma recognises several demographic "clusters" with heterogeneous clinical and physio-pathogenetic characteristics that are called "asthmatic phenotypes". Below are the two most representative asthmatic phenotypes:

allergic asthma: a more known and easier to identify asthmatic phenotype, characterised by eosinophilic inflammation and response to treatment with inhaled corticosteroid drugs;

non-allergic asthma: an asthmatic phenotype characterised by neutrophilic or eosinophilic inflammation, or containing a few inflammatory cells, which is distinguished by a poor response to treatment with inhaled cortisone. In particular, in preschool-aged children, viral infections are of considerable importance as a trigger factor for bronchospasm attacks.

In recent years, gut microbiota has been of great importance in the genesis of allergic and autoimmune diseases [2, 3]. An inadequate bacterial flora could be at the basis of immunological events that lead to the increase of pro-inflammatory cells (the cells that produce interleukins and cytokines in allergic phlogosis) that trigger the disease. The restoration of an appropriate bacterial flora can reduce or even delay the onset and worsening of such allergic and autoimmune diseases.

This is known for example from document U.S. Pat. No. 9,498,503. In such document, selected strains of probiotics are used for the treatment of allergic diseases, in particular for the treatment of atopic dermatitis. Specifically, this document regards a treatment to reduce and/or cure skin inflammation and/or to reduce symptoms such as redness of skin tissue, itching and eczema. Such treatment involves the administration of bacterial strains such as *Lactobacillus Salivarius* (LS01), *Bifidobacterium breve* (BR03), and *Lactobacillus pentosus* (LPS01). The study shows that such strains can be effective in the treatment of inflammatory skin diseases. However, the study reported in this document is not intended to treat and/or reduce the symptoms of asthma and dyspnoea, and nothing postulates or highlights this issue.

The use of strains of bacteria, *Lactobacillus salivarius* (LS01) and, *Bifidobacterium breve* (BR03) for the treatment of skin diseases is also known from the study of E. Nettis et al., Vol 48, N5, 182-187, 2016. Such document describes the use of the probiotic strains *Lactobacillus salivarius* LS01 and *Bifidobacterium breve* BR03 in the treatment of chronic spontaneous urticaria (see "Summary"). In detail, such study regards a group of adult patients, suffering from chronic spontaneous urticaria, and it shows that there is at least a partial remission due to the administration of the aforementioned strains of bacteria. The authors argue that evidence suggests that probiotic bacteria can modulate the immune system of the skin. The document reports that among patients who have shown a positive response to the treatment of chronic urticaria, some were also affected by allergic rhinitis. However, the does not address the treatment of allergic rhinitis problems in any manner and neither does it intend to treat the symptoms thereof. Neither does it mention the treatment of a respiratory disorder or ailment, possibly related to such allergic rhinitis.

In the light of the above, it is clear that there is a lack of indications on the ability of probiotics to intervene directly on the symptoms of respiratory disease, and on the reduction and/or resolution of asthma and dyspnoea events.

Asthma is a chronic inflammatory disease of the airways resulting from two major concomitant events: a spasm of the muscles surrounding the bronchi and the inflammation of the mucosa lining their internal. The combination of these two factors following an abnormal reaction to certain triggering factors causes the obstruction of bronchi hence preventing passage of air. This leads to the symptoms typical of people who suffer from asthma: lack or laboured breathing that causes annoying cough, a sense of tightness in the chest, wheezing, especially during the night or early morning. Acute obstruction of the lumen of the bronchi leads to an asthmatic attack. There are no symptoms in the interval between one attack and the other.

Previous studies (Drago et al.[4]), deriving from a previous in vitro test on a different formulation of bifidobacteria and lactobacilli, have demonstrated that on a specific cell model (PBMCs) this mixture of strains had the ability to modulate in vitro cytokine release by the immune system cells of adult allergic asthma patients. These data show that these probiotic strains have an anti-inflammatory action capable of inhibiting the Th2 cytokine profile which is increased in allergic pathologies, but without giving any indication on the ability of probiotics to intervene directly on the symptoms of the disease and on the resolution of the dyspnoea events. This important work therefore gives information on the resolution of inflammation, but not on the possible event of reduction of muscle spasm. Nevertheless, the current technique described above reveals some limits and drawbacks, in that it does not focus on reducing the greatest problem and discomfort for those suffering from asthma, i.e. on reducing the frequency and the intensity of dyspnoea events (breathing altered by rhythm and frequency, which occurs with fatigue or suffering by the patient).

Dyspnoea (shortness of breath) is the difficulty in breathing that may occur as temporary or chronic, gradual or sudden. Dyspnoea usually manifests itself as a laboured or as a bothersome sensation of not being able to catch breath.

The present invention falls within the above context, based on the previous assumptions, since the need to have a composition and a treatment for administration thereof which does not have the limitations and drawbacks of the compositions and pharmacological treatments traditionally used persists; said composition and treatment being capable of intervening in relation to the symptomatology of asthma and dyspnoea, and being well tolerated and easy to administer to all categories of subjects, including paediatric subjects.

More precisely, following extensive and intense research and development activity, the inventors of the present invention were able to identify and select, from among a very large group of species of bacteria and strains of bacteria, a specific strain of bacteria belonging to species B. *Breve* and a specific combination of strains of bacteria containing the same, showing synergistic characteristics effective in the treatment of a disease associated with an alteration of the respiratory airways, asthma and dyspnoea.

Forming an object of the present invention is an isolated strain of bacteria belonging to the species *Bifidobacterium breve* (B632) DSM 24706 for use in the treatment of a disorder or an ailment or a disease associated with an alteration of the respiratory airways, having the characteristics as defined in the attached claims.

Forming an object of the present invention is a mixture (m1) comprising or, alternatively, consisting of an isolated strain of bacteria belonging to the species *Bifidobacterium breve* (B632) DSM 24706 for use in the treatment of a disorder or an ailment or a disease of the respiratory airways, having the characteristics as defined in the attached claims.

Forming an object of the present invention is a composition (c1) comprising said mixture (m1) and, optionally, at least one physiologically and/or pharmacologically acceptable additive and/or technological excipient, having the characteristics as defined in the attached claims.

Forming an object of the present invention is a composition (c1) comprises said mixture (m1) and, optionally, at least one physiologically and/or pharmacologically acceptable additive and/or technological excipient, for use in the treatment of a disorder or an ailment or a disease associated with an alteration of the respiratory airways, having the characteristics as defined in the attached claims.

Forming an object of the present invention is a method for preparing mixtures (m1 and m2) and compositions (c1 and c2), having the characteristics as defined in the attached claims.

The present invention will now be described based on the attached figures, provided by way of nonlimiting example, wherein.

Figure 1:
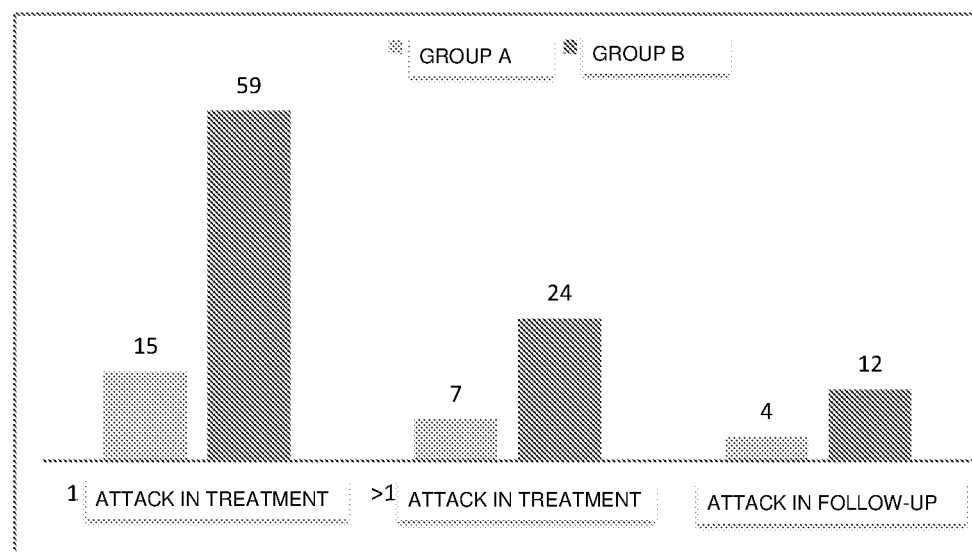
FIG. 1 is a column diagram exemplifying the number of asthmatic subjects included in the study, divided into subjects treated with the mixture (m2) of probiotics (Group A) or placebo (Group B); the treatment allowed to divide the patients into 3 distinct categories: those who had only one asthma attack during treatment, those who had more than one, and those who had asthma attack in the follow-up.

In the context of the present invention, the isolated strain of bacteria belonging to the species *Bifidobacterium breve* (B632) DSM 24706, the mixture, and the composition containing the same are for oral use.

In the context of the present invention, the isolated strain of bacteria belonging to the species *Bifidobacterium breve* (B632) DSM 24706, the mixture, and the composition containing the same are not for topical use, for example as topical gel.

In the context of the present invention, the expression: (i) "disease" is used to indicate the study of human diseases, in particular it is the field of medicine which studies the causes, development and effects of diseases, (ii) "ailment" refers to any pathological condition or alteration of the organism or of an organ thereof from an anatomical or functional point of view.

The disorder or ailment or disease is selected from among the group consisting of allergic rhinitis, respiratory difficulty, asthma (the two asthmatic phenotypes—allergic asthma and non-allergic asthma) and dyspnoea.

The Applicant selected and isolated a strain of bacteria belonging to the species *Bifidobacterium breve* deposited on 7 Apr. 2011, at Deutsche Sammlung von Mikroorganismen und Zellkulturen GmbH (DSMZ), such as *Bifidobacterium breve* (B632) and having accession number DSM 24706; such strain shows probiotic functional properties.

Advantageously, the isolated strain of bacteria *Bifidobacterium breve* (B632) DSM 24706, the mixture (m1) containing the same and the composition (c1) containing said mixture (m1) are capable of reducing the frequency and intensity of the dyspnoea events (respiration altered by rhythm and frequency, that occurs laboured or with suffering of the patient).

The Applicant successfully designed a study aimed at reducing the symptoms of both asthmatic phenotypes—allergic asthma and non-allergic asthma—described above.

Advantageously, the isolated strain of *Bifidobacterium breve* bacteria (B632) DSM 24706, the mixture (m1) containing the same and the composition (c1) containing said mixture (m1) are capable of reducing the symptoms of both asthmatic phenotypes—allergic asthma and non-allergic asthma.

The isolated strain of bacteria, subject of the present invention, belongs to the species *Bifidobacterium breve*. Said strain was deposited on 7 Apr. 2011, at Deutsche Sammlung von Mikroorganismen und Zellkulturen GmbH-DSMZ, as *Bifidobacterium breve* (B632) and it has accession number DSM 24706. Said strain is for paediatric use, it has prebiotic properties, and it is for use in the treatment of paediatric asthmatic subjects.

As regards the definition of "paediatric" or "paediatric age", in the present description these terms will refer to children aged from 1 day to 16 years, preferably from 1 year to 14 years.

Once prepared by means of a common fermentation process carried out using the apparatuses and methods known to those skilled in the art of fermentations, the isolated strain of *Bifidobacterium breve* bacteria (B632) DSM 24706 can be used as such, in solid flakes, powder, granules or freeze-dried form. Alternatively, said isolated strain may be mixed with an additive and/or a technological excipient (blending agent) such as inulin or maltodextrin.

Forming another object of the present invention is a mixture (m2) comprising, a or alternatively, consisting of (a) a strain of bacteria *Lactobacillus salivarius* (LS01) DSM 22775, deposited on 23 Jul. 2009 by Probiotical S.p.A. based in Novara (Italy) and (b) a strain of bacteria *Bifidobacterium breve* (B632) DSM 24706, deposited on 7 Apr. 2011 by Probiotical S.p.A. based in Novara (Italy) and, optionally, at least one physiologically and/or pharmacologically acceptable additive and/or excipient.

In this description, unless otherwise specified, the expressions "bacterial cultures", "bacterial strains" or "bacterial cultures subject of the invention" will be used for the sake of brevity to indicate a mixture—in desired ratios—comprising or, alternatively consisting of the bacterial culture *Lactobacillus salivarius* (LS01) DSM 22775, deposited on 23 Jul. 2009, and of the bacterial culture *Bifidobacterium breve* (B632) DSM 24706, deposited on 7 Apr. 2011.

It is known that strains of different bacteria belonging to the same species of bacteria can very often have different characteristics and behaviours. For this reason, the strains of the present invention show strain-specific distinctive features and behaviour.

Each of the bacterial cultures (a) and (b) can be considered to play the role and function of active ingredient in both the mixture and the composition containing the mixture (discussed below) of the scope of protection of the present invention.

The aforementioned bacterial cultures (a) and (b) are present in the mixture (m2) and in the composition (c2) containing said mixture (m2) at a *Lactobacillus salivarius* (LS01) DSM 22775: *Bifidobacterium breve* (B632) DSM 24706 by weight ration comprised from 1:4 to 4:1, advantageously comprised from 1:3 to 3:1, or comprised from 1:2 to 2:1; for example at a 1:1 by weight ratio.

The aforementioned bacterial cultures (a) and (b), considered individually, have a concentration comprised from $1\times10^{\wedge}6$ CFU/g to $1\times10^{\wedge}12$ CFU/g of culture. Considered individually, the aforementioned bacterial cultures are present in the mixtures (m1) and (m2) at a concentration comprised from $1\times10^{\wedge}7$ CFU/g to $1\times10^{\wedge}11$ CFU/g of mixture, for example at a concentration of about $1\times10^{\wedge}8$ CFU/g of mixture. The aforementioned bacterial cultures (a) and (b) are independently selected in the form of live and viable bacteria, dead bacteria or cell components thereof, cell extracts, lysates or tindalised thereof. The aforementioned bacterial cultures (a) and (b) are in solid form of powder, granules or flakes, or in frozen or freeze-dried form, preferably in the presence of at least one cryoprotector. The load is expressed in CFU/g or AFU/g.

According to an embodiment, in the mixtures (m1) and (m2) the strains of bacteria (a) and/or (b) and the physiologically and/or pharmaceutically acceptable acceptable additive and/or excipient could be present at a ratio by weight [bacterial strain/s:excipient/s] comprised from 1:4 to 4:1, advantageously comprised from 1:3 to 3:1, or comprised from 1:2 to 2:1, for example at a ratio of about 1:1. The percentage by weight of the strains of bacteria in the mixtures (m1) and (m2) could be comprised from 1% to 99% by weight, advantageously comprised from 40% to 99% by weight, or comprised from 60% to 99% by weight, with respect to the total weight of the mixture.

According to different embodiments, the at least one physiologically and/or pharmacologically acceptable excipient could be selected from among the group comprising a monosaccharide, a disaccharide, a polysaccharide, soluble fibres and/or insoluble fibres, GOS, FOS, inulin, maltodextrin and mixtures thereof.

According to different embodiments, the physiologically and/or pharmacologically acceptable excipient could be selected from among the group consisting of: inulin (CAS No. 9005-85-5), a fructooligosaccharide (FOS), Maltodextrin (CAS No. 9050-36-6) and mixtures thereof.

Forming an object of the present invention is a composition (c2) comprising a mixture (m2) comprising or, alternatively, consisting (at a desired ratio) of (a) a strain of bacteria *Lactobacillus salivarius* (LS01) DSM 22775, deposited on 23 Jul. 2009 by Probiotical S.p.A. based in Novara (Italy) and a strain of bacteria *Bifidobacterium breve* (B632) DSM 24706, deposited on 7 Apr. 2011 by Probiotical S.p.A. based in Novara (Italy) and, optionally, at least one physiologically and/or pharmacologically acceptable additive and/or excipient (for example a monosaccharide, a disaccharide, a polysaccharide, and mixtures thereof; or inulin (CAS No. 9005-85-5), a fructooligosaccharide (FOS), Maltodextrin (CAS No. 9050-36-6); and the physiologically and/or pharmacologically acceptable technological additive (or only one technological additive) (e.g. a preservative and/or stabilising substance).

Advantageously, the mixture (m2) and the composition (c2) containing said mixture (m2) are capable of reducing the frequency and intensity of the dyspnoea events (respiration altered by rhythm and frequency, that occurs laboured or with suffering of the patient).

Advantageously, the mixture (m2) and the composition (c2) containing said mixture (m2) are capable of reducing the symptoms of both asthmatic phenotypes—allergic asthma and non-allergic asthma.

According to an embodiment, in the aforementioned compositions (c1) and (c2) the by weight ratio [bacterial strain/s:excipient/s and/or additive/s] is comprised from 1:10 to 10:1, advantageously comprised from 1:5 to 5:1, or comprised from 1:2 to 2:1, for example at a ratio of about 1:1.

According to an embodiment, the percentage by weight of the mixtures in the aforementioned compositions (c1) and (c2) is comprised from 1% to 99% by weight, advantageously comprised from 40% to 99% by weight, or comprised from 60% to 99% by weight, with respect to the total weight of the composition.

According to an embodiment, the technological additive (or the plurality thereof) comprises or consists of a preservative substance and/or a stabilising substance.

According to an embodiment, the technological additive (or the plurality thereof) could be present at an additive: bacterial cultures ratio comprised between 0.1:30 and 1:1.

According to another embodiment, the technological additive (or the plurality thereof) could be present at an amount comprised from 0.1% to 50% with respect to the total weight of the composition, optionally at an amount comprised from 0.1 to 30% with respect to the total weight of the composition, advantageously at an amount comprised from 0.1% and 15% with respect to the total weight of the composition, for example comprised from 0.1% to 10% or comprised from 0.1% to 5% or comprised from 0.1% to 2% with respect to the total weight of the composition.

According to a further embodiment, the preservative substance and/or the stabilising substance comprises or consists of maltodextrin (CAS No. 9050-36-6). Maltodextrin is a water-soluble complex carbohydrate, obtained by chemical hydrolysis processes mainly from the breakdown of starch from cereals (corn, oats, wheat, rice) or tubers (potatoes, tapioca). According to an embodiment, maltodextrin or inulin are in solid form, for example in form of powder or granules.

By way of example, a maltodextrin usable according to the present invention is the product called Glucidex 19 powder maltodextrin, marketed by Roquette Italia SpA.

According to an advantageous embodiment, the culture of bacteria present in the mixtures and/or compositions subject of the invention can be combined or mixed in suitable proportions with the at least one physiologically and/or pharmaceutically acceptable technological additive, and optionally with at least one further culture of bacteria.

By way of example, such further culture of bacteria added in the mixtures of the present invention is selected from among the group consisting of:
  i) *Lactobacillus pentosus* (LPS01) DSM 21980, deposited on 14 Nov. 2008 by Probiotical S.p.A. based in Novara (Italy);
  ii) *Streptococcus thermophilus* (FP4) DSM 18616, deposited on 13 Sep. 2006 by Mofin S.r.l. based in Novara (Italy);
  iii) *Lactobacillus casei* ssp. *rhamnosus* (LR04) DSM 16605, deposited on 20 Jul. 2004 the Probiotical S.p.A. based in Novara (Italy);
  iv) *Lactobacillus acidophilus* (LA02) DSM 21717, deposited on 6 Aug. 2008 by Probiotical S.p.A. based in Novara (Italy); and
  v) combinations thereof.

It should be observed that the additional or optional cultures of bacteria are all deposited at Deutsche Sammlung von Mikroorganismen und Zellkulturen GmbH (DSMZ), Germany, according to the Budapest Treaty.

According to an embodiment of the present invention, the present composition is a composition for use as medicament or drug.

According to another embodiment, the present composition is a composition for use as medical device.

According to a further embodiment, the present composition is a composition for use as a dietary supplement.

According to a yet further embodiment, the present composition is a composition for use as a nutraceutical.

The aforementioned compositions are compositions for use in the treatment (preventive and/or curative) of at least one disorder or one ailment or one disease associated with an alteration of the respiratory airways and comorbidities associated therewith.

According to an embodiment, such disorder or ailment or disease is selected from among the group consisting of allergy, atopy, allergic rhinitis, food hypersensitivity, atopic dermatitis, eczema, respiratory difficulty and asthma or immunodeficiencies. In a preferred embodiment, the isolated strain of bacteria belonging to the species *Bifidobacterium breve* deposited on 7 Apr. 2011, at Deutsche Sammlung von Mikroorganismen und Zellkulturen GmbH (DSMZ), as *Bifidobacterium breve* (B632) and having accession number DSM 24706 is used in the treatment of a disorder or an ailment or a disease associated with an alteration of the immune system. Said disorder or ailment or disease associated with an alteration of the immune system is selected from among the group consisting of: allergy, atopy, allergic rhinitis, food hypersensitivity, atopic dermatitis, eczema, respiratory difficulty, asthma, or immunodeficiency.

According to a preferred embodiment, such a disease is a respiratory difficulty or asthma, particularly characterised by dyspnoea.

The compositions of the present invention are compositions for paediatric use, in particular it is for use in the treatment of paediatric asthmatic subjects.

According to a possible embodiment, the present composition is in liquid form, for example in the form of solution, suspension or dispersion.

According to another possible embodiment, the present composition is in solid form, for example in the form of powder or granules, or in the form of a tablet or pill.

Lastly, the above objectives are achieved through a method for preparing a mixture comprising at least one step of mixing the following isolated strains of bacteria deposited at Deutsche Sammlung von Mikroorganismen and Zellkulturen GmbH (DSMZ):
  *Lactobacillus salivarius* (LS01) DSM 22775, deposited on 23 Jul. 2009; and
  *Bifidobacterium breve* (B632) DSM 24706, deposited on 7 Apr. 2011;
  and optionally mixing at least one physiologically and/or pharmacologically acceptable excipient (or only one excipient) to obtain said mixture.

According to an embodiment, the mixing step is carried out dry, for example using bacterial cultures in powder form, for example freeze-dried form.

Since such method is preferably intended for the preparation of the mixture or of the composition described above, even if this is not explicit, such method could comprise any preferred or optional characteristic from among the ones outlined above.

Reported hereinafter are some examples of the present invention, provided by way of non-limiting example.

EXPERIMENTAL PART

Example 1: Experimental Part—Definitions and Method of Investigation

A double-blind randomised controlled study was conducted in a population of approximately 360 children with allergic asthma and recurrent dyspnoea, with the following objectives:
  a) main objective: to reduce the frequency and severity of asthmatic attacks or episodes of dyspnoea;
  b) secondary objectives: to reduce both the amount of drug administered for the treatment of asthma attack, and the duration of the basic treatment, leading to saving in terms of use of cortisone or other basic treatment drugs and ensuing reduction of pharmaceutical costs.

The observable asthma types (GINA 2016; [1], table 2) are as follows:
  intermittent asthma: with symptoms occurring less than once a week, nocturnal symptoms occurring less than twice a month, $FEV1>80\%$;
  mild persistent asthma: with symptoms occurring more than once a week but less than once a day, nocturnal symptoms more frequent than twice a month, $FEV1 \geq 80\%$;
  moderate persistent asthma: daily attacks limiting activity and sleep, nocturnal symptoms more frequent than once a week, $FEV1 \approx 60\text{-}80\%$;
  severe persistent asthma: daily attacks, frequent night symptoms limiting physical activities, $FEV1 \leq 60\%$.

It should be observed that the "FEV1" parameter indicated above (English acronym for "Forced Expiratory Volume in the 1st second") refers to the maximum expiratory volume in the first second of time. This is a parameter used in spirometry, which indicates the volume of air exhaled during the first second of a maximum forced expiration time, and it indicates the degree of patency of large airways. In the case of obstructive pulmonary bronchial diseases (e.g. asthma) the absolute value of FEV1 reduces, as it is closely related to the degree of bronchoconstriction.

The term "recurrent dyspnoea" is used to indicate symptoms that occurred in more than 3 episodes of dyspnoea in the previous year, in subjects aged from 6 months to 5 years, with negative prick tests (skin allergy test).

Regarding the severity of asthma attacks, the "Acute asthma severity classification" guidelines (SIP 2016; [5]) were used classifying attacks into:

Mild: the subject has the ability to speak normally, normal FRC (functional residual capacity), normal skin colour, normal sensory function, fine expiratory wheezing, no use of accessory muscles, normal FVC (forced vital capacity), FEV1>80%, Sat O2>95%;

Moderate: the subject can only say a few sentences, increased FRC, the child appears slightly agitated, pale skin colour, expiratory wheezing, moderate involvement of respiratory muscles, increased FVC, SatO2 comprised from 92-95%, FEV1 60-80%;

Severe: the subject says only a few words, pale/cyanotic skin colour, intense agitation, expiratory and inspiratory wheezing, remarkable involvement of the respiratory muscles, increased FVC, SatO2<92%, FEV1<60%.

Within the aforementioned population, the inclusion criteria used in the protocol of investigation were: children aged from 6 to 14 years, with mild persistent asthma and moderate asthma classified according to the GINA 2015 criteria outlined above, with negative or positive skin allergy tests (prick tests), as well as children of pre-school age with recurrent dyspnoea, with or without asthma diagnosis (positive and/or negative prick test).

The exclusion criteria were instead an age of the subject less than 1 year or greater than 14 years, subjects with severe persistent asthma, subjects with known congenital or acquired immunodeficiencies, subjects with cystic fibrosis and/or chronic lung diseases (e.g. bronchopulmonary dysplasia).

The population was selected by a group of eleven paediatricians, and it was divided into two different groups (A and B) with a corresponding number of subjects.

The mixture subject of the invention whose constituents are indicated in Table A was administered to Group A. A placebo composition whose constituents are reported in Table B was administered to group B.

TABLE A composition subject of the invention

| Strains of bacteria | Type | Declared load (MLD/dose) |
|---|---|---|
| *Lactobacillus salivarius* (LS01) DSM 22775 | bare (a)(LY)(b) | 1* |
| *Bifidobacterium breve* (B632) DSM 24706 | Bare (a) (LY)(b) | 1* |
| Maltodextrin (excipient) | / | / |

(a) Bare = uncoated cells
(b)LY = freeze-dried
*Theoretical load: 100 MLD/g.

TABLE B

| Placebo |
|---|
| Excipient |
| Maltodextrin |

Being a double-blind study, neither the paediatricians who administered the mixture and placebo (in short, the two compositions) listed in the previous tables, nor the patients who received it were aware of the nature of the composition administered, whether it was the composition of the invention (Table A) or the placebo composition (Table B).

Paediatricians reported the identification code of their patients with mild persistent allergic asthma and moderate asthma and recurrent dyspnoea, their age groups and, where applicable, whether they carried out the background therapy and for how long, with which drugs and protocol (expected duration).

The study was conducted for a total duration of 12 months, thus divided into two time periods:

A) Treatment with administration of a dose of composition, 1 sachet twice a day (morning and evening) for eight weeks, followed by 1 sachet once a day (morning or evening) for another eight weeks;

(B) Four-month follow-up to verify the effect of treatment on asthma attacks, recurrent wheezing (dyspnoea) and possible background therapy.

The severity of asthma attacks was evaluated using the SIP guidelines 2016 [5], based on clinical examination and saturation of O2 (saturometry) for subjects aged from 2 years to 5 years and 364 days.

Besides the clinical evaluation and saturation of O2, a spirometric evaluation was also performed for subjects aged from 6 years to 13 years and 364 days with the aim of evaluating FEV1 performance.

The same criterion was applied for follow-up (clinical examination, saturometry and spirometry) at the end of treatment for a period of four months, once a month if no attacks occurred. In such case, emergency outpatient visit (C1) and control was carried out at the end of the treatment of the attack (C2).

At the time of recruitment, paediatricians filled out a CRF (Case Report Form) in form of a table, containing the medical history and personal data of the recruited subjects: date of birth, age, sex, date of first examination, family atopy, familiarity and family environment (if the child lives in a town, city or mountain, warm/humid/dry environment, type of heating, passive smoke from mother or father (if so in number of cigarettes smoked at home and by whom)), siblings, education; personal allergic diathesis (such as positive prick tests, if present); number of asthmatic attacks or wheezing episodes in the previous year; FEV1 since last spirometry, where available. In another sheet, paediatricians also included data on any attacks that occurred during the active observation (treatment) and follow-up period (no treatment): severity of the attack, saturometry, and FEV1 of children admitted to the study. A third table reported data for subsequent examinations including: clinical examination, saturometry and FEV1 for children admitted to the study.

In conclusion, a visit was carried out at time T0 with subject recruitment and initiation of treatment (double-blind drug with placebo), a visit was carried out at time T1 at mid-treatment (about eight weeks from start), a visit at the end of the treatment at time T2 (16 weeks from the start).

The data collected at times T0, T1, T2 include clinical examination, saturometry and FEV1 for subjects who participated and, where applicable, background therapy.

Furthermore, the study included interim monthly evaluations in the follow-up period (time F1: after 1 month; time F2: after 2 months; time F3: 3 months after the end of treatment) with clinical examination, saturometry and spirometry for subjects who participated and, where applicable, increase or decrease or possible change in underlying therapies.

For example, in cases where the conditions of the children had deteriorated, an integration of cure with background therapy was required, or, in cases where the conditions of the children had improved, a suspension of background therapy was possible.

After the follow-up period, an examination was conducted at time FF, four months after the end of treatment.

Example 2: Statistical Analysis of the Results Obtained in Example 1

The statistical analysis was conducted by Centro Studi Scientifico SIMPE. The statistical analysis involved all randomized children. The incidence and/or prevalence of acute asthma attacks were evaluated, and any differences between group A and group B were compared by means of Student's t test and the Adjusted Relative Risk (ARR) for confounding patterns, using the MedCal Ostend Belgium, and Epi info 7 software.

The statistical analysis was conducted calculating:
(a) Relative risk (RR), statistical significance (SS), Number Needed to Treat (NNT), for variables that included a reduction in asthma attacks during treatment or follow-up;
b) T test for correlating the ACT (Asthma Control Test) trend of the children during the treatment according to the present invention.

The first data which markedly stands out is the significant—statistically significant—reduction in asthma attacks during treatment with respect to the placebo, as simplified in Table C below, whose numerical values are shown in the diagram in FIG. 1:

TABLE C

Number of attacks in treatment (1 attack, or >1 attacks), and in follow-up.

| GROUP (No. of subjects) | 1 ATTACK | RR/ SS/ NNT | >1 ATTACK | RR/ SS/ NNT | ATTACKS IN FOLLOW-UP | RR/ SS/ NNT |
|---|---|---|---|---|---|---|
| A(160) | 15 | 0.2/ <0.0001/ 3 | 7 | 0.3/ 0.01/ 12 | 4 | 0.3/ 0.1/ 26 |
| B(189) | 59 | | 24 | | 12 | | wherein: RR = relative risk; SS = statistical significance; NNT = Number Needed to Treat.

The reduction of attacks is obviously accompanied by a reduction in the administration of medicines to overcome the attack, where such reduction in the number of attacks also regards the second attack. However, this effect of reducing the number of attacks is transitory, and it is lost over time from the end of treatment.

A further important fact is the significant improvement—during treatment—of the quality of life of the asthmatic child regardless of the background therapy, as can be seen from the improvement in the ACT that was conducted.

Figure 2:
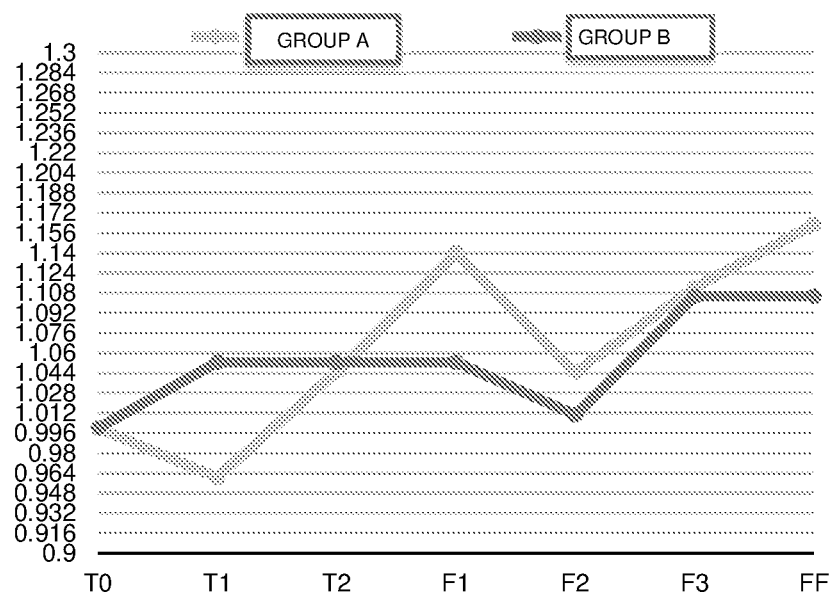
FIG. 2 is a diagram that exemplifies an improvement in FEV1 as a function of time in Group A patients compared to Group B patients.

With regard to spirometry data—exemplified in FIG. 2—spirometry in children highlights an increase in FEV1 parameter, and thus a reduction in the degree of bronchoconstriction, since the start of treatment. This improvement is also maintained in follow-up.

The data shown in FIG. 2 correspond to the numerical values of the following Table D.

TABLE D

FEV1 values in groups A and B.

| | T0 | T1 | T2 | F1 | F2 | F3 | FF |
|---|---|---|---|---|---|---|---|
| GROUP A | 1 | 0.96 | 1.04 | 1.14 | 1.04 | 1.11 | 1.16 |
| GROUP B | 1 | 1.05 | 1.05 | 1.05 | 1.01 | 1.11 | 1.11 |

The embodiments of the isolated strain for use, of the mixture, of the composition, of the aforementioned uses and of the method can be subjected—by a man skilled in the art—to substitutions or modifications to the described characteristics depending on the contingencies. These embodiments are also to be considered included in the scope of protection formalised in the following claims.

Furthermore, it should be observed that any embodiment may be implemented independently from the other embodiments described.

BIBLIOGRAPHIC REFERENCES

[1] Global Strategy for Asthma Management and Prevention, Global Guidelines (2016 update).
[2] S. BIBBÓ (1,2), G. IANIRO (1), V. GIORGIO (3), F. SCALDAFERRI (1), L. MASUCCI (4), A. GASBARRINI (1), G. CAMMAROTA (1); (1): Internal Medicine, Gastroenterology and Liver Unit, Catholic University of the Sacred Heart, School of Medicine, A. Gemelli Foundation, Rome, Italy; (2): Department of Clinical and Experimental Medicine, University of Sassari, Italy; (3): Division of Pediatrics, Catholic University of the Sacred Heart, School of Medicine A. Gemelli Foundation, Rome, Italy; (4): Institute of Microbiology, Catholic University of the Sacred Heart, A. Gemelli Foundation, School of Medicine, Rome, Italy; Corresponding Author: Stefano Bibbó, MD; e-mail: s.bibbo@gmail.com The role of diet on gut microbiota composition European Review for Medical and Pharmacological Sciences 2016; 20: 4742-4749.
[3] Stitaya Sirisinha: The potential impact of gut microbiota on your health: Current status and future challenges.
[4] Drago L. et all. Immunomodulatory Effects of *Lactobacillus salivarius* LS01 and *Bifidobacterium breve* BR03, Alone and in Combination, on Peripheral Blood Mononuclear Cells of Allergic Asthmatics Allergy Asthma Immunol Res. 2015 July; 7(4):409-413.
[5] SIP (Societá Italiana di Pediatria) guidelines for acute asthma attack, rev. 2016.

The invention claimed is:

1. A method for treating a disorder or ailment or disease of the respiratory airways of a subject in need thereof, comprising
administering to the subject an effective amount of an isolated strain *Bifidobacterium breve* (B632) deposited under accession number DSM 24706.

2. The method according to claim 1, wherein said disorder or ailment or disease of the respiratory airways of the individual is selected from the group consisting of allergic rhinitis, respiratory difficulty, asthma and dyspnoea.

3. The method according to claim 1, wherein said isolated strain *Bifidobacterium breve* (B632) is administered at a concentration ranging from $1\times10^6$ CFU/g to $1\times10^{12}$ CFU/g.

4. The method according to claim 1, wherein said isolated strain *Bifidobacterium breve* (B632) is administered as a bacterial culture of whole and/or viable living cells, as a bacterial culture of non-viable cells or components, as cell extracts, or as cell lysates.

5. The method according to claim 1, wherein said isolated strain *Bifidobacterium breve* (B632) is administered at a concentration ranging from $1\times10^8$ CFU/g to $1\times10^{10}$ CFU/g.

6. The method according to claim 1, wherein said isolated strain *Bifidobacterium breve* (B632) is administered at a concentration of about $1\times10^9$ CFU/g.

7. The method according to claim 1, wherein said isolated strain *Bifidobacterium breve* (B632) is administered as a bacterial culture of non-viable cells, as cell components, as cell extracts, or as cell lysates.

8. The method according to claim 1, wherein said isolated strain *Bifidobacterium breve* (B632) is administered within a composition further comprising at least one physiologically and/or pharmacologically acceptable technological additive or excipient.

9. The method according to claim 8, wherein said technological additive is selected from the group consisting of a preservative substance and/or a stabilising substance.

10. The method according to claim 8, wherein said pharmacologically acceptable excipient comprises maltodextrin or inulin.

* * * * *